Figure 1:
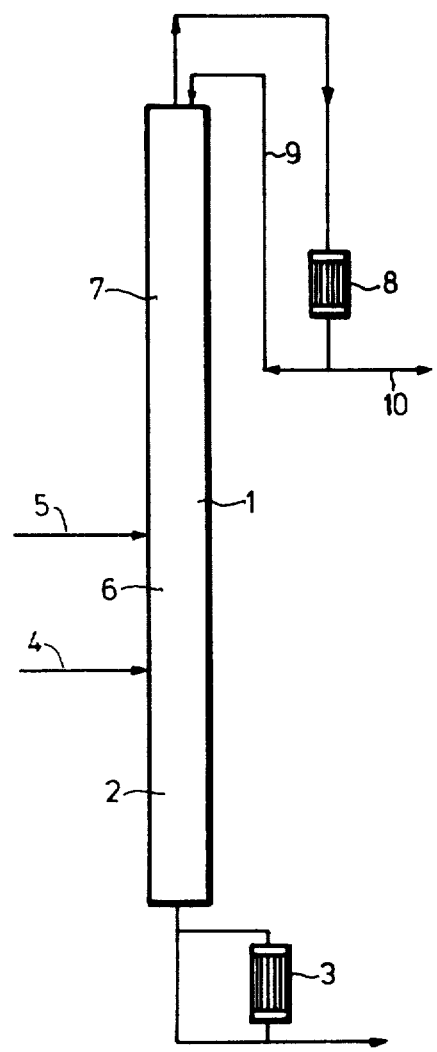

United States Patent [19]

Seifert et al.

[11] 4,369,096
[45] Jan. 18, 1983

[54] PROCESS FOR THE PURIFICATION OF EPOXIDES

[75] Inventors: Hermann Seifert, Cologne; Helmut Waldmann, Leverkusen; Rolf Wirthwein, Hanau; Willi Hofen, Rodenbach, all of Fed. Rep. of Germany

[73] Assignees: Bayer Aktiengesellschaft, Leverkusen; Deutsche Gold und Silberscheideanstalt Vormals Roessler, Frankfurt am Main, both of Fed. Rep. of Germany

[21] Appl. No.: 179,316

[22] Filed: Aug. 18, 1980

Related U.S. Application Data

[63] Continuation of Ser. No. 13,758, Feb. 21, 1979, abandoned.

[30] Foreign Application Priority Data

Mar. 11, 1978 [DE] Fed. Rep. of Germany ....... 2810662

[51] Int. Cl.³ .................................................. B01D 3/34
[52] U.S. Cl. ........................................ 203/58; 203/59; 203/63; 203/67; 203/69; 203/70
[58] Field of Search ................. 203/58, 59, 63, 68–70, 203/67, 91, 51; 260/348.34, 348.37, 348.18, 348.36; 560/860

[56] References Cited

U.S. PATENT DOCUMENTS 3,149,131  9/1964  Bartlett ........................... 260/348.37
3,597,452  8/1971  Laemmle et al. .............. 260/348.34

FOREIGN PATENT DOCUMENTS 681866  12/1935  Fed. Rep. of Germany .
2047292  9/1970  Fed. Rep. of Germany .

OTHER PUBLICATIONS

Chemical Abstracts, vol. 71, Nr. 17, 27-10-1969, Nr. 81128p, Columbus, Ohio, U.S.A., H. Ouchi et al.: "Purification of alkylene oxides", Seite 372, linke Spalte and JP-A-69 09650 (Mitsui Toatsu Chem. Ind.).

*Primary Examiner*—Frank Sever
*Attorney, Agent, or Firm*—Sprung, Horn, Kramer & Woods

[57] ABSTRACT

A process has been developed for the purification of expoxides containing carbonyl compounds as impurities wherein the carbonyl compound content is up to 2% by weight of epoxide. Purification is effected by treatment with compounds containing at least one $NH_2$ group.

20 Claims, 1 Drawing Figure

PROCESS FOR THE PURIFICATION OF EPOXIDES

This is a continuation of application Ser. No. 013,758, filed Feb. 21, 1979 now abandoned.

The present invention relates to an improved process for the purification of epoxides or mixtures containing epoxides. The present invention particularly relates to the removal of compounds containing carbonyl groups from epoxides or from mixtures in which epoxides are present. Epoxides such as ethylene oxide, propylene oxide, butylene oxide, styrene oxide, epichlorohydrin or glycidol are important intermediate products which have a broad application in the plastics field, for example in polyurethanes, or in the field of adhesives.

Quantitatively, epoxides of lower olefins, for example ethylene oxide and propylene oxide, are by far the most important monomeric compounds of this type. In view of the quality of the end products, a very high purity of these epoxides is required. In particular, compounds which contain carbonyl groups, for example the aldehydes, ketones and esters containing, in each case, 1 to 5 C atoms, may be present in epoxides only in very low concentrations. Thus it is necessary, for example, to keep the concentration of acetaldehyde in propylene oxide to below 50 ppm, since at higher acetaldehyde contents coloured products are formed, for example in the preparation of polyethers from epoxides. In the following text, it is essentially explained, using propylene oxide as an example, how numerous the proposals which have been made for removing the compounds mentioned are, as a result of the high purity required of the product.

All the preparation processes hitherto known for low-molecular epoxides are based on oxidation of the corresponding olefin. Chlorine in association with an alkali, molecular oxygen, organic hydroperoxides or percarboxylic acids are used as oxidising agents in these processes. Electrochemical processes have also been disclosed. By-products which contain oxygen in the form of carbonyl groups are formed to a greater or lesser extent in all these processes. In the case of the preparation of propylene oxide, examples of by-products which are observed are formaldehyde, acetaldehyde, acetone, propionaldehyde and esters of low-molecular carboxylic acids, for example methyl formate. These troublesome by-products are formed not only by oxidative degradation of the propylene, but can also be formed from propylene oxide during the reaction or during working up of the reaction mixtures. A number of purification processes, which are based either on a physico-chemical preparation operation or on a chemical reaction, has already been proposed for removing the by-products containing carbonyl groups from the propylene oxide.

Distillation is used as the physico-chemical separation operation for the purification of epoxides. However, in most cases only the extractive distillation processes, that is to say processes which are carried out with the aid of an additional solvent in counter-current, give sufficiently satisfactory results.

To separate off methyl formate from propylene oxide it is proposed, for example, according to German Patent Specification No. 1,224,293, to carry out an extractive distillation using hydrocarbons. Hydrocarbons such as olefins, aromatics and mixtures thereof are described, in U.S. Pat. No. 3,337,425, as suitable extraction agents for separating off impurities which contain oxygen and which boil within a range of plus or minus 5° C. from the boiling point of the epoxide, from the epoxide by extractive distillation. Methyl formate and acetaldehyde are mentioned as compounds to be separated off from propylene oxide.

In U.S. Pat. No. 2,622,060, an aqueous, alkaline solution is recommended as an extraction agent, so that impurities such as acetaldehyde and methyl formate can be removed from propylene oxide by means of an extractive distillation. This procedure in the presence of aqueous alkali gives rise to high losses of epoxide, since, as is known, epoxides undergo saponification to glycols in the presence of aqueous alkali. Moreover, it is possible to separate off water from propylene oxide only with a very high expenditure on distillation (see DT-OS (German Published Specification) No. 2,015,602). Apart from the disadvantages which can arise from the losses of epoxide, all extractive distillation processes for separating off carbonyl compounds from propylene oxide are expensive, since at least one further distillation unit is required so that the extraction agent can be purified and can be recycled as free from losses as possible. The fact that the extraction agent used contaminates the olefin oxide is to be regarded as a further, not inconsiderable disadvantage.

It is not possible to separate off the impurities mentioned, containing carbonyl groups, from propylene oxide by simple distillation with a sufficiently satisfactory result, although this could in fact have been expected from the considerable differences in the boiling points of these compounds. The difficulties observed are partly connected with the formation of azeotropic mixtures with boiling points close to that of propylene oxide. Separating off the lower aldehydes is to be regarded as particularly difficult. In this context, in Dt-OS (German Published Specification) No. 2,454,115 (page 2, paragraph 3) it is stated that the separating off of aldehydes—which in general are present in amounts of up to about 2% by weight—is a problem since a propylene oxide which is satisfactory for industrial purposes should contain less than about 100 ppm, and preferably less than about 20 ppm, of aldehydes, expressed as propionaldehyde.

With respect to the propylene oxide losses which occur during simple separation of acetaldehyde and propylene oxide by distillation—that is to say without using an extraction agent—it is mentioned in DT-OS (German Published Specification) No. 2,454,115 (page 3, paragraph 2) that about 30% of the propylene oxide in the acetaldehyde-containing distillate which is obtained in the course of the isolation of propylene oxide is lost.

In order to decrease these losses, it is proposed, in DT-OS (German Published Specification) No. 2,454,115, to separate off the aldehydes acetaldehyde and propionaldehyde individually in two distillation units, acetaldehyde first being obtained as the distillate. In addition to the great expense, as a result of using columns with 90 and 62 trays respectively and high reflux ratios, the double exposure to heat which the propylene oxide undergoes in the presence of not inconsiderable amounts of water is to be regarded as a further significant disadvantage.

Other processes which have hitherto been disclosed for removing impurities containing carbonyl groups from epoxides se chemical auxiliaries in order to purify the epoxides by binding carbonyl compounds. However, they have such considerable disadvantages that application to industrial processes is eliminated in all cases.

It is proposed, in U.S. Pat. No. 3,816,478, to remove formaldehyde, acetaldehyde or propionaldehyde from the propylene oxide by treatment with solid sodium bisulphite. In order to carry out this process, the sodium bisulphite is arranged in a fixed bed and the impure propylene oxide is passed over this bed, addition compounds being formed from the sulphite and the aldehydes. The organic feed product used in the purification must contain about 2% by weight of water. Conversions of the epoxide proceeding, to a considerable degree, as side-reactions are, above all, to be regarded as disadvantages of the process. Moreover, the epoxide to be purified contains sulphur dioxide as an impurity. When the surfaces of the bisulphite granules are coated with the aldehyde addition compound, the fixed bed must be purified by rinsing with an inert, organic solvent and then treated with air or nitrogen at a relatively high temperature. Apart from the necessity of setting up a second washing tower which exists in the case of a continuous procedure, these two process steps adversely affect the process considerably and make the carrying out thereof appear to be of little advantage.

A further process for removing compounds containing carbonyl groups from propylene oxide is proposed in British Patent Specification No. 1,035,866. Chemical modification of the impurities is carried out by means of sodium borohydride. This compound has the advantage of reacting selectively with the compounds containing carbonyl groups, but also has serious disadvantages. Thus, in the reaction of sodium borohydride with aldehydes, ketones and esters, boron-containing organic compounds are formed which are essentially insoluble and make expensive filtering devices necessary in the case of carrying out the process industrially. Sodium borohydride itself is in turn soluble in propylene oxide to a small extent, which leads to deposits and blockages in pipes and heat exchangers during the subsequent distillation.

A further method for the purification of propylene oxide using chemical agents is described in Japanese Laid-Open Specification No. 9650/69 (Chemical Abstracts 71, 81128 p (1969)). The use of aqueous solutions of hydrazine is proposed for removing propionaldehyde from propylene oxide. A disadvantage of this process is that reaction times of twenty hours are necessary at room temperature in order to obtain quantitative reaction of the propionaldehyde. Reaction times of this order can be realised industrially only at considerable expense since very large reactor volumes must be available in the case of these residance times. Moreover, as a result of these long reaction times, losses of propylene oxide also occur, caused by the side-reaction, which also takes place and is now not inconsiderable, of the propylene oxide with the hydrazine or with the water of the hydrazine solution. The fact that when this process is used for removing acetaldehyde from propylene oxide products are formed which have only a very low solubility in the epoxide to be purified, so that expensive measures must be taken when carrying out the process industrially in order that no deposits and blockages caused by these insoluble products occur in evaporators, apparatuses and pipelines, is to be regarded as a further disadvantage of the process according to this Japanese Laid-Open Specification No. 9650/69.

The process according to Japanese Laid-Open Specification No. 9650/69, with the disadvantages and limitations described above, is thus suitable only for removing propionaldehyde. If, for example, acetaldehyde, as the only carbonyl compound present in the mixture, is to be removed from a mixture containing propylene oxide, it is necessary, in order to by-pass the difficulties caused by the formation of insoluble products, to also add propionaldehyde—as a solubilising agent as it were—to the mixture, in addition to the acetaldehyde already present. However, the addition of propionaldehyde simultaneously also means a higher consumption of aqueous hydrazine solution.

All of these processes which utilise a chemical reaction for removing impurities containing carbonyl groups from epoxides have the common disadvantage that the required reagent, employed in excess, as well as the reaction products formed from the reagent and the compounds containing carbonyl groups, are additional impurities. In addition to the reaction step which is automatically necessary, subsequent separation of the reaction mixture by distillation is therefore unavoidable. In most cases this distillation is made more difficult, if not absolutely impossible, by the formation of mixtures of complicated composition which boil azeotropically with the epoxide.

Summarising, on the processes hitherto disclosed for the purification of epoxides, in particular of propylene oxide, to remove carbonyl compounds it can thus be said that none of these processes presents a satisfactory solution to this problem.

In contrast, an industrially simple and economically advantageous process for the purification of epoxides has been found, which is characterised in that the epoxide, or an epoxide-containing mixture, which contains, relative to the epoxide, up to 2% by weight of carbonyl compounds containing 1 to 5 C atoms, is passed into the middle region of a distillation unit, a compound which contains one or more unsubstituted $NH_2$ groups is passed in above the inlet of the epoxide-containing product stream and the purified epoxide is taken off as the top product, or in a side stream, above the point at which this compound containing at least one $NH_2$ group enters the distillation column.

This process can be carried out, for example, by a procedure in which a distillation unit is used which contains a stripping section with 1 to 50 theoretical plates, a concentrating section with 1 to 70 theoretical plates, a vaporiser unit and a condensing device, the epoxide or the epoxide-containing mixture being passed in between the stripping section and concentrating section, the compound with the unsubstituted $NH_2$ group being passed in 1 to 20 theoretical plates above this point and the purified epoxide being taken off as the top product, or in a side stream, 1 to 50 theoretical plates above the feed point of the compound containing the unsubstituted amino group. The process according to the invention can advantageously be carried out by a procedure in which, for example, ethylene oxide, propylene oxide, 1,2-epoxybutane, 2,3-epoxybutane, vinyloxirane or styrene oxide or a mixture which contains one of these epoxides, the epoxide or the epoxide-containing mixture containing, relative to the epoxide, up to 2% by weight of carbonyl compounds containing 1 to 5 C atoms, is fed into a distillation unit which consists of a stripping section with 1 to 20 theoretical plates, a concentrating section, a vaporiser unit and a condensing device, the compound with the unsubstituted $NH_2$ group being passed in 1 to 10 theoretical plates above the inlet for the epoxide or the epoxide-containing mixture and the purified epoxide being taken off as the top product, or in a side stream, 5 to 40 theoretical plates above the inlet for the compound containing the $NH_2$ group, under an overhead pressure of 0.01 to 2.5 bars and at a ratio of reflux onto the column to distillate removed at the top of 0.1 to 10:1.

Possible distillation units which can be used for the process according to the invention are customary columns, such as tray columns or packed columns. Columns which are provided with wire gauze packings or glass fibre fabric packings or with ceramic packings are also suitable. The section of the column between the two inlet points advantageously takes the form of a tray column.

The known vaporiser designs, such as thin film vaporisers, falling film vaporisers, circulatory vaporisers or climbing film vaporisers can be employed as the vaporiser. In general, circulatory vaporisers are quite suitable.

Materials which can be employed for constructing the entire distillation tower, the vaporiser and the condenser are the construction materials usually used for this purpose in chemical plant construction, for example steel, glass, high-grade steels and enamelled steels.

The epoxides which can be purified in an advantageous manner by the process according to the invention are monoepoxides and polyepoxides with 2 to 20 C atoms, preferably with 2 to 10 C atoms, in particular the monoepoxides and diepoxides of lower olefins, for example of olefins with 2-6 C atoms, such as ethylene oxide, propylene oxide, butylene oxide (1,2-epoxybutane and 2,3-epoxybutane), isobutylene oxide and vinyloxirane (butadiene monoepoxide) or epoxides of olefins substituted by chlorine, aryl and hydroxyl, such as epichlorohydrin, glycidol, 1,2-dichloro-3,4-epoxybutane, 1,4-dichloro-2,3-epoxybutane, styrene oxide or 1,2-diphenylethylene oxide. The process according to the invention can be particularly advantageously employed for the purification of ethylene oxide and propylene oxide, and of 1,2-epoxybutane and 2,3-epoxybutane. The process according to the invention can be very particularly advantageously employed for the purification of propylene oxide.

The stream, containing the epoxide, introduced into the distillation unit can consist predominantly of epoxide or can be a solution of the epoxide, it being possible for up to 2% by weight of carbonyl compounds to be present, relative to the epoxide. If the epoxide employed is used in the form of a solution, possible product streams are those which are obtained during the separation of the reaction mixtures in the preparation of epoxides by industrial processes. Preferred possible solvents for the epoxide employed are thus those which are used in the preparation processes for the epoxides. Examples of such solvents are ethylbenzene, methylphenylcarbinol, benzene, toluene, acetic acid, tert.-butyl alcohol, water and dichloropropane, and mixtures of these compounds. The amount of solvent diluting the epoxide can vary within wide limits, for example from 10 to 90% by weight, and is of no particular importance for the process according to the invention.

Examples of the impurities, containing carbonyl groups, which usually make it difficult to isolate the epoxides in the pure form and can be removed using the process according to the invention are aldehydes, ketones and esters, which contain 1 to 5 C atoms in the molecule in each case, such as formaldehyde, acetaldehyde, propionaldehyde, acetone, acrolein, diacetyl, methyl ethyl ketone, hydroxyacetone, butyraldehyde, crotonaldehyde, methyl formate, acetic acid methyl ester, acetic acid isopropyl ester and propionic acid ethyl ester. In general, these compounds have boiling points below that of the epoxide being purified. However, carbonyl compounds which have a higher boiling point than the epoxide but which form, with the epoxide and if appropriate water, an azeotrope which has a boiling point lower than that of the epoxide or close to the boiling point of the epoxide can also be successfully separated off by the process according to the invention, as can carbonyl compounds which have boiling points lower than that of the epoxide and which form an azeotrope, which in some cases contains considerable amounts of epoxide, below the boiling point of the epoxide. It is a particular advantage of the process according to the invention that the epoxides can be separated off in a simple manner from mixtures in which aldehydes, ketones and esters of lower carboxylic acids which have a very different chemical structure are simultaneously present in varying concentration. Thus, for example, it is possible to separate formaldehyde, acetaldehyde, acrolein, propionaldehyde, acetone and methyl formate from propylene oxide in one distillation step without difficulty and without detectable losses of propylene oxide thereby occurring.

In the process according to the invention, the compound which contains one or more unsubstituted $NH_2$ groups in the molecule is fed into the distillation unit at the point indicated. Virtually any chemical compound which contains at least one $NH_2$ group in its molecule can be used for this.

Individual examples of compounds of this type which are suitable for carrying out the process according to the invention are: monoamines of the general formula R—$NH_2$, R being a substituted or unsubstituted aliphatic (particularly alkyl or hydroxyalkyl) radical in the straight-chain or branched form or an aromatic (particularly phenyl or naphthyl unsubstituted or substituted on the aromatic nucleus by $C_1$–$C_4$-alkyl, nitro etc) radical, such as, for example, ethylamine, n-propylamine, isopropylamine, n-butylamine, isobutylamine, and ethanolamine, or aniline, toluidine, o-nitroaniline and $\alpha$- or $\beta$-naphthylamine. Further amines which can be used for the process according to the invention are: diamines which have alkylene radicals with, for example, two or three C atoms or a phenylene radical between the two $NH_2$ groups in the molecule, such as, for example, ethylenediamine, 1,2-diaminopropane, 1,3-diaminopropane or o-phenylenediamine; but also aminals, acid amides of carboxylic acids (particularly $C_1$–$C_6$-alkane carboxylic acids), sulphonic acids (particularly $C_1$–$C_6$-alkane-sulphonic acids, benzene sulphonic or naphthalene sulphonic acids, etc.) or phosphonic acids (particularly $C_1$–$C_6$-alkane phosphonic acids), such as, for example, acetamide, propionamide, isobutyramide, benzenesulphonamide, p-toluenesulphonamide and the amide of the monomethyl ester of methylphosphonic acid, or amides of carbonic acid, such as urea or N-alkyl- or N,N-dialkyl-urea (particularly in which each alkyl group contains up to 6 carbon atoms); aminocarboxylic acids, particularly $\alpha$-aminocarboxylic acids, such as glycine, alanine, norvaline methionine, valine and lysine, as well as anthranilic acid or the nitriles of $\alpha$-aminocarboxylic acids, for instance those named above, such as, for example, $\alpha$-amino-propionitrile, are also suitable. In addition to amines and amides, cyanamide or hydroxylamine and hydrazine and hydrazine derivatives which contain an unsubstituted $NH_2$ group are also suitable for the process according to the invention. Examples which may be mentioned are hydrazine, hydrazine monohydrate, monoalkyl (particularly $C_1$–$C_6$-alkyl) hydrazines, such as methyl-, ethyl-, propyl-, butyl- and isopropylhydrazine, arylhydrazines (particularly phenylhydrazines which are unsubstituted or substituted by $C_1$–$C_6$-alkyl or nitro), such as phenylhydrazine and 2,4-dinitrophenylhydrazine, dialkylhydrazines, such as N,N-dimethylhydrazine, and hydrazides (particularly $C_1$–$C_6$-alkyl carboxylic acid or benzoic acid hydrazides), such as semicarbazide, acetohydrazide, benzoic acid hydrazide, isobutyric acid hydrazide and hydrazides of thiocarboxylic acid.

In addition to the compounds with the free $NH_2$ groups in the molecule, the corresponding salts of mineral acids and carboxylic acids can also be employed, such as, for example, the ammonium salts of the compounds, containing $NH_2$ groups, listed which are derived from hydrochloric acid, sulphuric acid and acetic acid. Examples which may be mentioned are tert.-butylamine hydrochloride, the bisulphate of 1,2-diaminoethane or also hydrazinium salts, such as hydrazine sulphate.

n-Alkylamines with 2 to 5 C atoms, amides and hydrazides of carboxylic acids with 1 to 5 C atoms and hydroxylamine hydrochloride may be mentioned as being particularly suitable for the process according to the invention.

1,2-Diaminoalkanes with 2 to 5 C atoms, aniline, phenylhydrazine, N,N-dimethylhydrazine and hydrazine hydrate and very particularly suitable.

Compounds containing $NH_2$ groups which are solid under normal conditions are advantageously fed to the distillation column as a solution in an inert solvent. Liquid monoamines or diamines, amides or derivatives of hydrazine are in general introduced into the column in the undiluted form.

Suitable solvents which can be used for the compounds with $NH_2$ groups which are in the form of solids are higher-boiling esters, chlorinated hydrocarbons, aromatics, ethers, water and phosphorus-containing compounds. Benzene, toluene, ethylbenzene and xylenes are particularly suitable. It is very particularly advantageous to use dioxane or other cyclic ethers, or phosphoric acid esters, such as tributylphosphate. In general, in establishing the system epoxide to be purified/compound containing $NH_2$ group/solvent, the difference in the boiling points of the epoxide and solvent is also taken into consideration, in addition to the solution properties with respect to the compound which contains the amino group. For the process according to the invention, it is favourable to choose a solvent which has a boiling point at least 20° C. higher than that of the epoxide. In general, solvents which have boiling points at least 50° C. higher than that of the epoxide are quite suitable. A solvent which has a boiling point between 60° and 110° C. higher than that of the epoxide is advantageously used.

The concentration of the compound containing the $NH_2$ group in the solution being employed in the distillation column can be varied within wide limits, depending on the nature of the solvent. In general, contents of 0.1 to 90% by weight are quite suitable. These concentrations are advantageously 20 to 80% by weight, and very particularly preferably 30 to 70% by weight.

The amount of the compound containing the amino group which is generally used for the process according to the invention depends on the content of carbonyl compounds in the epoxide to be purified. However, it can vary within wide limits. A molar ratio of the compound containing the $NH_2$ group to carbonyl compounds of 0.5:1 is in most cases already sufficient. A range from 1 to 5:1 is advantageously chosen for this molar quotient. It is very particularly advantageous to establish a molar ratio of the compound containing the $NH_2$ group to carbonyl compounds of 1 to 3:1.

In addition to monoamines and diamines, acid amides or hydrazine and hydrazine derivatives, in general it is also possible to use, for the process according to the invention, other compounds which are capable of reacting with carbonyl compounds, such as, for example so-called CH-acid compounds: nitromethane, dimedone, malonic acid dialkyl esters and acetylacetone.

The pressure in the distillation unit used in the process according to the invention can be, for example, 0.01 to 2.5 bars. The pressure is appropriately chosen so that the purified epoxide obtained in the upper section of the column can be condensed with cooling water of, for example, 25° C. The pressure conditions in the section of the distillation unit between the feed points of the epoxide and amino compounds or the solution of the compounds containing the $NH_2$ group are also determined by choosing the pressure in the column. At the same time, however, since the boiling point of the epoxide at the given pressure is fixed, the temperatures in this section of the column are also determined roughly. Depending on which epoxide is to be purified, that is to say which temperature would be set up at the top of the column under 1 bar, the pressure in the column is thus chosen so that temperatures of between 10° and 150° C., preferably of 20° to 100° C. and very particularly preferably of 30° to 80° C., are set up in that part of the column which is defined by the feed points for the epoxide and amino compound or the solution of the compound containing the $NH_2$ group and which preferably comprises 1 to 10 theoretical plates. If the section of the column defined by the feed points is more than one theoretical plate, for example 5 plates, in general a temperature difference is set up between the lowest plate and the uppermost plate. In this case, the extreme temperatures found in this section of the column, that is to say the highest temperature and the lowest temperature, should be in the temperature ranges indicated above.

The reflux ratio under which the distillation unit of the process according to the invention is operated can be, for example, 0.1 to 10:1, this ratio being understood as the ratio of the amount of reflux onto the column to the amount of distillate removed at the top.

The reflux ratio can be more or less than that indicated. For example, it is also possible to carry out the distillation at considerably higher reflux ratios.

The purified epoxide obtained as the top product, or in a side stream, by the process according to the invention contains less than 100 ppm of carbonyl compounds, calculated as acetaldehyde. This content is preferably less than 50 ppm, and particularly preferably less than 20 ppm.

In addition to the isolation of purified epoxide, it is also possible, if the epoxide fed into the distillation unit is in the form of a mixture, to isolate all or some of the compound functioning as the solvent as the top product, together with the epoxide. In this case also, the mixtures of purified epoxide and solvent then obtained have the abovementioned specifications.

A preferred way of carrying out the process according to the invention is described in the following text, using the purification of propylene oxide as an example, is depicted in FIG. 1.

A distillation unit (1) is used, the stripping section (2) of which, that is to say the section of the column below (4), comprises 5 to 8 theoretical plates. The column is heated by a circulatory vaporiser (3). The column section (6) between the inlet for a solution containing propylene oxide in ethylbenzene (4) and the inlet for the solution containing n-butylamine (5) comprises 3 to 6 theoretical plates, which are realised by about 5 to 8 actual trays, in the form of bubble trays. The section (7) of the distillation unit above the feed point (5) of the n-butylamine solution consists of 15 to 20 theoretical plates and is in the form of a packed column section containing glass Raschig rings. The propylene oxide passing over the top is condensed in the heat exchanger (8). The reflux onto the column is effected via line (9). The distillation unit (1) is charged through line (4) with a solution containing 10 to 25% by weight of propylene oxide in ethylbenzene. In addition to propylene oxide and ethylbenzene, this feed stream (4) also contains 0.5 to 1.5% by weight of acetaldehyde, 0.1 to 0.8% by weight of propionaldehyde, 0.05 to 0.25% by weight of methyl formate, 0.01 to 0.2% by weight of acrolein, about 1% by weight of water and traces of acetone. A solution which contains 40 to 50% by weight of n-butylamine and 20 to 30% by weight of water in methanephosphonic acid dimethyl ester is fed to the column via line (5). The molar ratio of n-butylamine to carbonyl compounds is 1.1 to 2.5:1. The distillation unit is operated under a pressure of 1.0 to 1.5 bars. The reflux ratio is 5 to 8:1. In the section of the column designated by (6), the temperature is 50° to 70° C. Purified propylene oxide is obtained at the top of the column and, after being condensed, is discharged via line (10). This product contains less than 50 ppm of carbonyl compounds. The water content is below 100 ppm. Nitrogen-containing compounds cannot be detected.

The advantages of the process according to the invention can be summarised as follows:

(1) High purity of the epoxide obtained;

(2) Low technical effort because of simple process measures, which can be called novel countercurrent reactive distillation;

(3) Negligible loss of epoxide;

(4) Removal of all the troublesome carbonyl compounds in one distillation column, whilst at the same time there is the possibility of separating off the epoxide from a solvent in the same column;

(5) Applicability of the process even to cases where a compound which contains carbonyl groups and is an impurity in the epoxide is liberated from another compound by exposure to heat during the distillation.

(6) Isolation of pure epoxide, the solvent and the carbonyl compounds being separated off in a single distillation column (compared with at least two distillation columns, as are necessary to achieve similar results, for example in the process according to DT-OS (German Published Specification) No. 2,454,115).

EXAMPLES (SEE ALSO FIG. 1)

EXAMPLE 1

A distillation unit, exclusively in the form of a bubble tray column, with a diameter of 5 cm and a stripping section comprising 10 actual trays and a concentrating section consisting of a total of 25 actual trays is charged via line (4) with 250 ml per hour of 98.5% pure vinyloxirane (density: 0.87), which contains 1.2% by weight of carbonyl compounds and 0.3% by weight of butenediols and butenediol monoacetates as well as small amounts of water. This product stream is prewarmed to 65° C. before entering the column. The column is provided with a circulatory vaporiser and, at the top, with a condenser and a distillate tank. In detail, the 1.2% by weight of carbonyl compounds consist of the following compounds: 0.5% by weight of crotonaldehyde, 0.1% by weight of acetaldehyde, 0.25% by weight of methyl ethyl ketone, 0.08% by weight of propionaldehyde and 0.27% by weight of acrolein. A 35% strength by weight solution of semicarbazide in dioxane is introduced, in an amount of 13.4 g per hour, into the column via line (5) five actual trays above the inlet (4) into the column for the vinyloxirane, that is to say at the level of the 15th actual tray in total, calculated from the sump. The molar quotient of semicarbazide to carbonyl compounds is thus thus 1.5:1.

The column is operated under an overhead pressure of 1 bar. The reflux ratio is 5:1, so that about 1.23 l per hour of vinyloxirane are recycled onto the column via (9). The overhead temperature set up is 68° to 69° C. The temperature between the 13th and 14th tray is about 70° to 72° C.

214 g per hour of vinyloxirane, which has a purity of 99.95%, is removed from the distillate tank via (10). The content of carbonyl compounds is below 50 ppm.

Comparison of the streams of material (4) and (10) shows that the loss of vinyloxirane is only 0.5%, which is virtually within the accuracy of measurement.

EXAMPLE 2

A distillation column which has a diameter of 5 cm over its entire length is used. The stripping section consists of a glass column section 50 cm long packed with 4×4 mm glass Raschig rings, whilst the concentrating section is composed of a tube containing from 4 bubble trays and a further tube which is packed with high-grade steel wire mesh rings. The bubble tray column section is immediately above the feed point for the product. The column section packed with the wire mesh rings, which has a length of 1.5 m, follows this column section, in the upward direction. The column is heated by a falling film vaporiser. 450 ml per hour of styrene oxide (density: 1.06), which is prewarmed to 70° C. before entering the column, are introduced into the column, which is operated under a pressure of 0.015 bar (overhead pressure). The styrene oxide has a purity of 99.2% by weight. The impurities consist essentially of acetone, acetaldehyde and methyl ethyl ketone, acetone, with 0.6% by weight, being the main constituent of the impurities containing carbonyl groups. In addition to these impurities, the styrene oxide also contains 0.12% by weight of water.

The feed point for a 25% strength by weight solution of acetohydrazide in tributyl phosphate is at the upper end of the column section containing four bubble trays. 25 g per hour of this solution are introduced into the column.

The reflux ratio is 1:1 and the temperature at the top of the column is 71°–72° C. 470 g per hour of styrene oxide, of which the content of carbonyl compounds is below 100 ppm, are obtained as the top product. No loss of styrene oxide can be detected.

EXAMPLE 3

A product stream which contains, in addition to benzene, 32.5% by weight of propylene oxide, 0.4% by weight of propylene glycol, 0.1% by weight of acetaldehyde, 0.05% by weight of methyl formate and 0.01% by weight of acetone as well as 0.3% by weight of water is introduced, in an amount of 300 ml per hour, into a distillation column which is provided with a total of 45 bubble trays. The column, which has a diameter of 5 cm, is heated by a circulatory vaporiser.

The inlet into the column for the stream containing propylene oxide is between the 15th and 16th tray, calculated from the sump. 0.92 g per hour of a 64% strength by weight aqueous solution of hydrazine is introduced between the 25th and the 26th tray. A molar ratio of carbonyl compounds to hydrazine of 1.3:1 thus results.

The column is operated under an overhead pressure of 1.33 bars. The overhead temperature is 43°–44° C. and the reflux ratio is 7:1. The top vapours are condensed with cooling water.

Propylene oxide is removed from the column as the distillate in an amount of 169 ml per hour. The product obtained contains less than 10 ppm of acetaldehyde and less than 200 ppm of water. Methyl formate and acetone can no longer be detected.

290 g per hour of benzene are discharged as the bottom product. The bottom product contains less than 0.01% by weight of propylene oxide.

EXAMPLE 4

A mixture which contains, in addition to ethylbenzene, 45.2% by weight of propylene oxide, 0.08% by weight of acetaldehyde, 0.01% by weight of methyl formate and 0.05% by weight of propionaldehyde as well as 0.5% by weight of water and small amounts of propylene glycol is introduced, in an amount of 450 g per hour, into a distillation column which has a diameter of 5 cm and is provided with 50 bubble trays. The product feed, that is to say the introduction of the solution of propylene oxide in ethylbenzene, into the column, which is heated by a falling film vaporiser, is at the level of the 20th tray, calculated from the sump. 17 g per hour of a 10% strength by weight solution of n-butylamine in dioxane are fed to the column between the 30th and 31st tray, also counted from the sump. The molar ratio of amine to carbonyl compounds is 1.8:1. The column is operated under normal pressure. 244 ml per hour of propylene oxide are obtained as the distillate at an overhead temperature of 34° C. and a reflux ratio of about 6.5:1. This product now only contains 10–15 ppm of acetaldehyde. The content of other carbonyl compounds is below 50 ppm.

EXAMPLE 5

The 2,3-trans-butylene oxide to be purified is in the form of a solution in tert.-butanol. The epoxide content is 70.2% by weight. 0.15% by weight of methyl ethyl ketone, 0.1% by weight of n-butyraldehyde and 0.08% by weight of propionaldehyde as well as traces of acrolein and water are also present in the solution. A packed column 2.5 m long and 4.5 cm in diameter, which is packed with 4×4 mm glass rings up to a middle section containing 5 bubble trays, is used as the distillation column. The inlet for the product stream, prewarmed to 55° C. and containing 2,3-trans-butylene oxide, is below the bubble tray column section, whilst a 35% strength by weight solution of phenylhydrazine in dioxane is introduced at the upper end thereof, still before the start of the upper packed column section.

The solution containing the epoxide is introduced into the column in an amount of 350 ml per hour and the solution of phenylhydrazine in dioxane is introduced in an amount of 9.5 g per hour, so that the molar ratio of carbonyl compounds to phenylhydrazine is 2.2:1. The column is operated under normal pressure. The reflux ratio is 5:1. 237 ml per hour of 2,3-trans-butylene oxide, which contains less than 50 ppm of carbonyl compounds, are obtained as the distillate at an overhead temperature of 56°–57° C. Tert.-butanol is removed from the column as the bottom product.

EXAMPLE 6

The epoxide to be purified is again 2,3-trans-butylene oxide. The distillation column used has the dimensions indicated in Example 5. The product-containing stream is likewise again introduced below the column section containing the bubble trays. The butylene oxide to be separated off is in the form of a solution in benzene, which has the following composition. 23.3% by weight of 2,3-trans-butene oxide, 0.15% by weight of n-butyraldehyde, 0.12% by weight of methyl ethyl ketone and 0.2% by weight of diacetyl and small amounts of water.

This solution is introduced into the column in an amount of 300 g per hour. 1.7 ml per hour of ethylenediamine are introduced into the column at the upper end of the column section containing the bubble trays.

The column is operated under normal pressure. 68.5 g per hour of a 2,3-butylene oxide, which contains less than 100 ppm of carbonyl compounds, are obtained as the distillate at an overhead temperature of 57° C. and a reflux ratio of 9:1.

What is claimed is:

1. A process for the purification of epoxides which comprises passing a feed stream consisting essentially of epoxide alone or in admixture with a solvent used in its preparation which feed stream contains relative to the epoxide, up to 2% by weight of carbonyl compounds containing 1 to 5 C atoms, into the middle region of a distillation unit, passing in a compound which contains one or more $NH_2$ groups above the inlet of the epoxide-containing feed stream and taking off the purified epoxide as the top product, or in a side stream, above the point at which said compound containing at least one $NH_2$ group entering the distillation column so that the carbonyl content is reduced distillatively to less than 100 ppm.

2. A process according to claim 1 wherein a distillation unit is used which contains a stripping section with 1 to 50 theoretical plates, a concentrating section with 1 to 70 theoretical plates, a vaporiser unit and a condensing device, the epoxide or the epoxide-containing mixture being passed in between the stripping section and the concentrating section, the compound containing at least one free $NH_2$ group being passed in 1 to 20 theoretical plates above this point and the purified epoxide being taken off as the top product, or in a side stream, 1 to 50 theoretical plates above the feed point.

3. A process according to claim 1 wherein ethylene oxide, propylene oxide, 1,2-epoxybutane, 2,3-epoxybutane, vinyloxirane or styrene oxide or a mixture which contains one of the said epoxides, said epoxide or epoxide-containing mixture containing, relative to the epoxide, up to 2% by weight of carbonyl compounds containing 1 to 5 C atoms, is fed into a distillation unit which consists of a stripping section with 1 to 20 theoretical plates, a concentrating section, a vaporiser unit and a condensing device, a compound with an unsubstituted NH$_2$ group being passed in 1 to 10 theoretical plates above the inlet for the epoxide or the epoxide-containing mixture and the purified epoxide being taken off as the top product, or in a side stream, 5 to 40 theoretical plates above the inlet for the compound containing an NH$_2$ group, under an overhead pressure of 0.01 to 2.5 bars and at a ratio of reflux onto the column to distillate removed at the top of 0.1 to 10:1.

4. A process according to claim 3 wherein propylene oxide or mixtures containing propylene oxide are employed as the epoxide.

5. A process according to claim 1 wherein the column section between the two feed points is in the form of a tray column.

6. A process according to claim 1 wherein an epoxide-containing mixture which contains ethylbenzene, methylphenylcarbinol, toluene, xylene, benzene, tert.-butyl alcohol or dichloropropane is passed in.

7. A process according to claim 1 wherein a monoamine of the formula R—NH$_2$ in which R is an optionally substituted aliphatic or aromatic radical, a C$_1$- to C$_3$-alkylenediamine, a phenylenediamine, an animal, an acid amide of a carboxylic acid, sulphonic acid or phosphonic acid, urea or an N-alkyl or N,N-dialkyl-urea, an aminocarboxylic acid, anthranilic acid, cyanamide or hydroxylamine is employed as the compound with an unsubstituted NH$_2$ group.

8. A process according to claim 1 wherein hydrazine, hydrazine hydrate, a monoalkylhydrazine, an N,N-dialkylhydrazine, a monoarylhydrazine, hydrazides and/or hydrazinium salts are employed as the compound with an unsubstituted NH$_2$ group.

9. A process according to claim 8 wherein hydrazine, hydrazine hydrate, monoalkylhydrazine, N,N-dialkylhydrazines, monoarylhydrazines, hydrazides and/or hydrazinium salts are employed in the form of a 30 to 70% strength by weight solution.

10. A process according to claim 8 wherein an aqueous, 40 to 70% strength by weight solution of hydrazine is employed.

11. A process according to claim 8 wherein the hydrazine or the hydrazine derivative is employed in an amount that the molar quotient of hydrazine or hydrazine derivative to carbonyl compound is 1 to 3:1.

12. A process according to claim 1 wherein a temperature of 30° to 80° C. is set up in the column section defined by the two feed points.

13. A process according to claim 1 wherein the distillation unit is operated under an overhead pressure of 0.1 to 2.5 bars.

14. A process according to claim 1 wherein the epoxide removed contains less than 100 ppm of carbonyl compounds.

15. A process according to claim 1, wherein the epoxide is in admixture with a solvent.

16. A process according to claim 15, wherein said solvent is selected from the group consisting of ethylbenzene, methylphenyl carbinol, benzene, toluene, acetic acid, tert-butyl alcohol, water and dichloropropane.

17. A process according to claim 15, wherein said solvent is selected from the group consisting of ethylbenzene, methylphenyl carbinol, benzene, toluene, acetic acid, tert-butyl alcohol and dichloropropane.

18. A process according to claim 17, wherein the solvent is present in an amount of 10 to 90 percent by weight.

19. A process according to claim 1, wherein the carbonyl compound is an aldehyde ketone or ester which contains 1 to 5 carbon atoms in the molecule.

20. A process according to claim 19, wherein said carbonyl compound is selected from the group consisting of formaldehyde, acetaldehyde, propionaldehyde, acetone, acrolein, diacetyl, methyl ethyl ketone, hydroxyacetone, butyraldehyde, crotonaldehyde, methyl formate, acetic acid methyl ester, acetic acid isopropyl ester and propionic acid ethyl ester.

* * * * *